(12) United States Patent
Andersson et al.

(10) Patent No.: US 8,481,298 B2
(45) Date of Patent: Jul. 9, 2013

(54) SEPARATION MATRIX FOR VIRAL PURIFICATION

(75) Inventors: Inger Andersson, Storvreta (SE); Andreas Axen, Jarlasa (SE); Peder Bergvall, Uppsala (SE); John Clachan, Uppsala (SE); Camilla Estmer-Nilsson, Uppsala (SE); Lena M. Sandberg, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 273 days.

(21) Appl. No.: 12/442,957

(22) PCT Filed: Sep. 26, 2007

(86) PCT No.: PCT/SE2007/000852
§ 371 (c)(1),
(2), (4) Date: Mar. 26, 2009

(87) PCT Pub. No.: WO2008/039136
PCT Pub. Date: Apr. 3, 2008

(65) Prior Publication Data
US 2010/0099163 A1    Apr. 22, 2010

(30) Foreign Application Priority Data
Sep. 29, 2006  (SE) ........................ 0602060

(51) Int. Cl.
*C12N 7/02* (2006.01)
*C12N 7/00* (2006.01)
*A61K 39/145* (2006.01)

(52) U.S. Cl.
USPC ........................ 435/239; 435/235.1

(58) Field of Classification Search
None
See application file for complete search history.

(56) References Cited

U.S. PATENT DOCUMENTS

| 4,724,210 | A | * | 2/1988 | Oka et al. ................ 435/239 |
| 5,447,859 | A |   | 9/1995 | Prussak |
| 6,537,793 | B2 |  | 3/2003 | Blanche et al. |
| 6,602,990 | B1 |  | 8/2003 | Berg |
| 2002/0037565 | A1 | | 3/2002 | Blanche et al. |
| 2003/0187227 | A1 | | 10/2003 | Lihme et al. |
| 2005/0059086 | A1 | | 3/2005 | Huang et al. |

FOREIGN PATENT DOCUMENTS

| EP | 0 679 436 | 11/1995 |
| EP | 0679436 B1 * | 6/2000 |
| EP | 0 848 752 | 6/2003 |
| GB | 1 511 997 | 5/1978 |
| WO | WO 97/15661 | 5/1997 |
| WO | WO 98/26048 | 6/1998 |

OTHER PUBLICATIONS

Pepper, D., et al., "Chromatography of Human Prothrombin Complex of Dextran Sulphate Agarose" Thrombosis Research, vol. 11, No. 5, 687-692 (1977).
Database WPI Week 200160, Thomson Scientific, London, GB; and JP 2001 190273 (JSR Corp.) Jul. 17, 2001; Abstract.
"Heparin as pseudo affinity chromatography ligand in influenza virus purification," IP.com Journal, Sep. 18, 2006, IP.com identification No. IPCOM000140661D.
Extended EP Search Report Issued on Corresponding Application No. 07808848.1 Dated Nov. 28, 2011.

* cited by examiner

*Primary Examiner* — Mary E Mosher
*Assistant Examiner* — Myron Hill

(57) ABSTRACT

The present invention relates to a method of preparing a separation matrix comprising at least one insoluble carrier to which sulphate ligands have been attached via extenders, which method comprises coupling, in a first step, of the sulphate ligands to the extenders and, in a subsequent step, attaching the extenders to an insoluble carrier. The invention also relates to a separation matrix comprised of at least one insoluble carrier to which sulphate ligands have been attached via extenders. Advantageously, no sulphate ligands are directly attached to the insoluble carrier. The extenders may be natural polymers, such as dextran, and the insoluble carrier may be made from natural polymers, such as agarose, or synthetic polymers. The invention also relates to a method of purifying virus, such as influenza virus, using a separation matrix according to the invention.

6 Claims, 2 Drawing Sheets

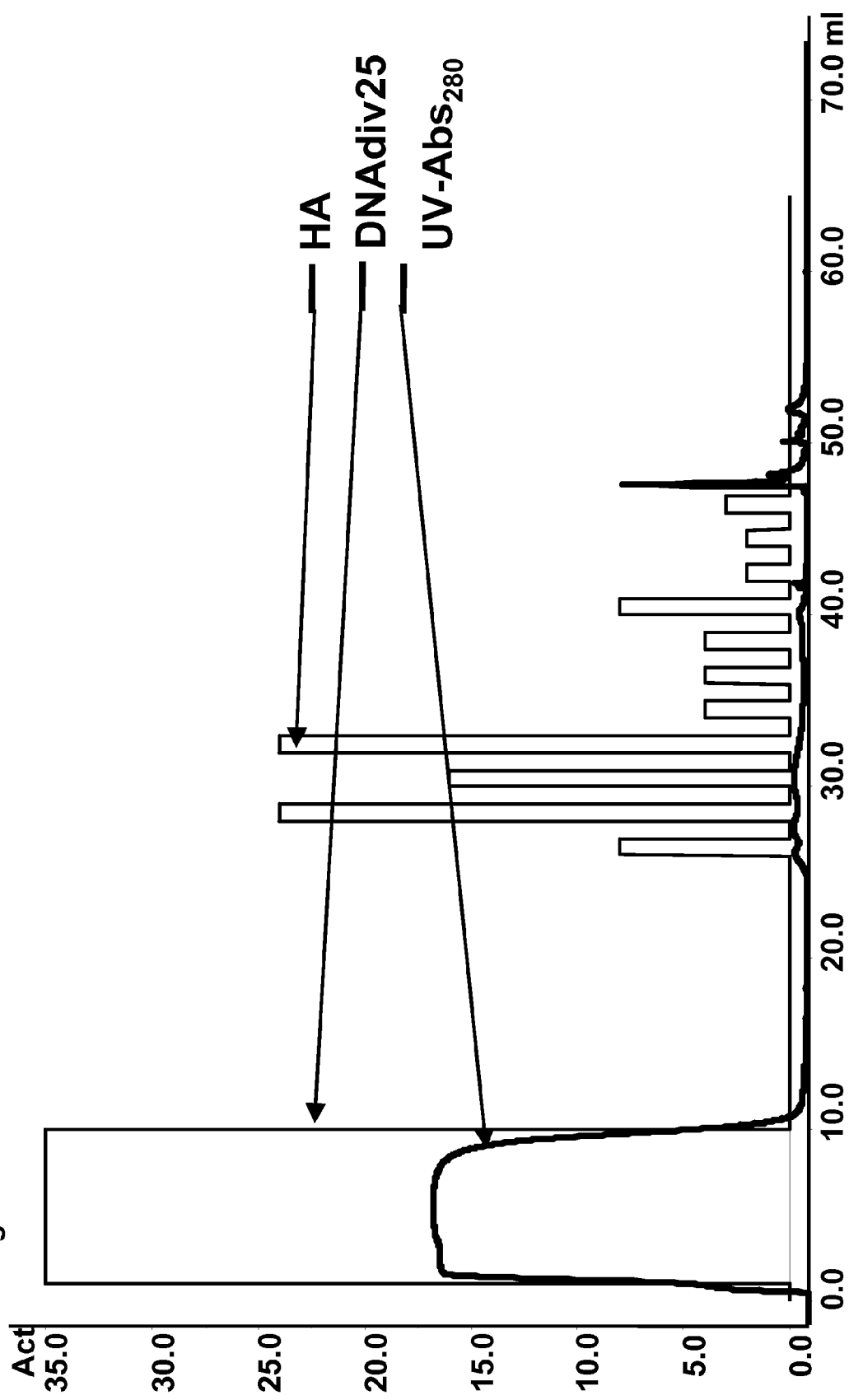

SEPARATION MATRIX FOR VIRAL PURIFICATION

CROSS-REFERENCE TO RELATED APPLICATIONS

This application is a filing under 35 U.S.C. §371 and claims priority to international patent application number PCT/SE2007/000852 filed Sep. 26, 2007, published on Apr. 3, 2008, as WO 2008/039136, which claims priority to patent application number 0602060-6 filed in Sweden on Sep. 29, 2006.

FIELD OF THE INVENTION

The present invention relates to a new separation matrix; which is suitable for the purification of virus. In addition, the invention also encompasses a method of preparing such a separation matrix as well as a method of viral purification using the separation matrix according to the invention. Most preferably, the virus separated is influenza virus, such as human influenza virus.

BACKGROUND OF THE INVENTION

Viruses are ultramicroscopic infectious agents, comprised of a piece of nucleic acid (DNA or RNA) wrapped in a thin coat of protein, which replicate only within cells of living hosts. As many are pathogenic; there is a widespread need to remove viruses from biological products such as fluids, especially for use in the medical and diagnostic field. In addition, the relatively new field of gene therapy, wherein virus is used as carriers of genes intended for therapeutic applications, also requires procedures for the purification of virus. Finally, research directed to the virus vaccine field also requires availability of efficient methods of purifying virus. For example, the recent outbreak of avian flu in some parts of the world resulted in increased research efforts directed to the finding of an efficient vaccine.

WO 9826048 (Schering Corporation) relates to virus purification by anion exchange followed by size exclusion chromatography. More specifically, this patent application discloses a method for purification of a virus preparation comprising:

a) subjecting the virus preparation to anion exchange chromatography, wherein the virus is eluted from an anion-exchange chromatographic medium; and b) subjecting the virus product of step A to size exclusion chromatography, wherein the virus is eluted from a size exclusion chromatographic medium.

EP 0 848 752 (Aventis Pasteur) relates to purification of viruses by cation and ion exchange chromatography. More specifically, this patent application relates to a method for purifying virus obtained from a cell culture, which consists in separating by ion-exchange chromatography the viruses from the cell proteins and DNA originating from the culture, characterized in that it comprises at least one step of anion exchange chromatography and one step of cation exchange chromatography. In one embodiment, the viruses purified are influenza viruses.

U.S. Pat. No. 6,537,793 (Aventis) relates to viral purification, and more specifically to viral purification on an ion exchanger to which ligands have been coupled to a matrix via extenders. The matrix may be chosen from agarose, dextran, acrylamide, silica and poly[styrene-divinylbenzene], preferably, the matrix consists of agarose. Advantageously, the flexible arm is of a hydrophilic nature and consists of a polymer of synthetic or natural origin. Among the polymers of synthetic origin, polymers consisting of monomers of polyvinyl alcohols, polyacrylamides, polymethacrylamides or polyvinyl ethers are mentioned. By way of polymer of natural origin, in particular polymers of a polysaccharide nature chosen from starch, cellulose, dextran and agarose are suggested. Preferably, the flexible arm is functionalized by grafting a group capable of interacting with an anionic molecule, such as a ternary or quaternary amine. It is stated to be particularly advantageous to use a strong anion exchanger. A support presented as being particularly preferred is Q SEPHAROSE™ XL (GE Healthcare, Uppsala, Sweden), which is an agarose base matrix to which Q groups have been attached via dextran.

WO 97/15661 (Allen) relates to a microporous pathogen-killing composition. More specifically, a microporous substance is disclosed, wherein the pores are sized to permit entry of pathogenic particles but exclude blood cells, and a singlet oxygen-generating system is bound to the microporous substance. In a particular embodiment, a ligand that binds a pathogenic particle is also bound to the microporous substance, which ligand may be selected among high mannose glycans, N-glucosamine, the N-acetylglucosaminyl core of oligosaccharides, the monosyl core of complex-type N-linked glycans, mannan, α-methylmannoside, haloperoxidases, sulphated polysaccharides, low molecular weight dextran sulphate, and lectins. The preferred ligands include the haloperoxidase myeloperoxidase and the lectin concavalin A.

US 2003/0187227 (Lihme) relates to the isolation of immunoglobulins from a solution containing immunoglobulins, e.g. hybridoma cell culture supernatants, animal plasma or sera, and to a solid phase matrix useful in said isolation. More specifically, the solid phase matrix comprises a functionalised matrix backbone carrying a plurality of functional groups of the formula: M-SP1-L, wherein M designates the matrix backbone; SP1 designates a spacer and L designates a ligand comprising a mono- or bicyclic optionally substituted aromatic or heteroaromatic moiety. In one embodiment, the ligand comprises at least one nitrogen, sulphur or phosphorus atom, such as a ring atom or as a substituent on the heteroaromatic ring, such as an amino or nitro group or a sulfonic acid group or a phosphonic acid group.

U.S. Pat. No. 5,447,859 (Prussak) relates to a method for the purification or removal of retroviruses using sulphated cellulose. More specifically, moderately to highly sulphated oligosaccharides are stated to be useful for a variety of purposes, including the purification of viruses, the removal of vital contaminants in preparations, and the delivery of viruses. In this context, "moderately sulfated" refers to oligosaccharides having at least about 6-15 μmoles sulphate per gram of oligosaccharide; and "highly sulfated refers to greater than about 15 μmoles sulphate per gram of oligosaccharide. Generally, in this disclosure, the maximum level of sulfation is stated to be about 20 μmoles per gram. Suitable oligosaccharides include alkyl oligosaccharides, with cellulose, heparin and agarose as preferred oligosaccharides.

U.S. Pat. No. 4,724,210 (Oka et al) relates to a method for the purification of influenza virus, which comprises subjecting a solution containing the influenza virus to column chromatography using, as a gel for chromatography, a sulfuric acid ester of cellulose or a crosslinked polysaccharide. The method can provide highly purified influenza virus which is useful for obtaining an effective vaccine against influenza. The sulfuric acid ester of a crosslinked polysaccharide used includes a sulfuric acid ester of polysaccharide, such as dextran, cellulose, or agarose, which is crosslinked with a crosslinking agent. Further, the gel for chromatography is characterized in that it is prepared by directly sulfating cellulose or a crosslinked polysaccharide, which are water-insoluble, with a sulfating agent such as chlorosulfonic acid or anhydrous sulfuric acid in an organic solvent, e.g. pyridine. Thus, the resultant gel is water-insoluble and highly stable.

However, despite the above-discussed methods, there is an increasing demand for optimized and generic products for the purification of virus, especially for the purification of influenza virus.

SUMMARY OF THE INVENTION

One aspect of the invention is to provide a method of preparing a separation matrix suitable for the purification of virus, such as influenza virus.

Another aspect of the present invention is a separation matrix as such, which is suitable for the purification of virus, such as influenza virus.

A further aspect of the invention is to provide a method of purifying virus from a liquid, such as a biological fluid, e.g. a cell culture supernatant.

A specific aspect of the invention is to provide a method of separating virus, such as influenza virus, from nucleic acids such as DNA and RNA.

These and other aspects may be achieved as defined in the appended claims. Further aspects and advantages of the invention will appear from the detailed description and examples that follow below.

BRIEF DESCRIPTION OF THE DRAWINGS

In FIG. 1 (and FIG. 2), "Cond" (---) means conductivity in mS/cm in the buffer; UV-Abs (+++) denotes the adsorption at 280 nm; HA (///) denotes the target virus concentration determined as hemaglutinine activity; DNAdiv25 (×××) denotes the nucleic acid concentration; ELISA×20 (\\\) denotes the target virus concentration determined by a conventionally used ELISA method.

FIG. 2 shows the chromatogram obtained when virus was purified on a prototype separation matrix according to the invention (prototype U1404038), as described in example 1 below. In FIG. 2, the same symbols as in FIG. 1 are used denoting the separate curves. As appears from a comparison of the FIGS. 1 and 2, the separation of target virus from DNA obtained by use of the prototype according to the invention is well comparable to the separation obtained by the commercially available cellulose product.

DEFINITIONS

Figure 1:
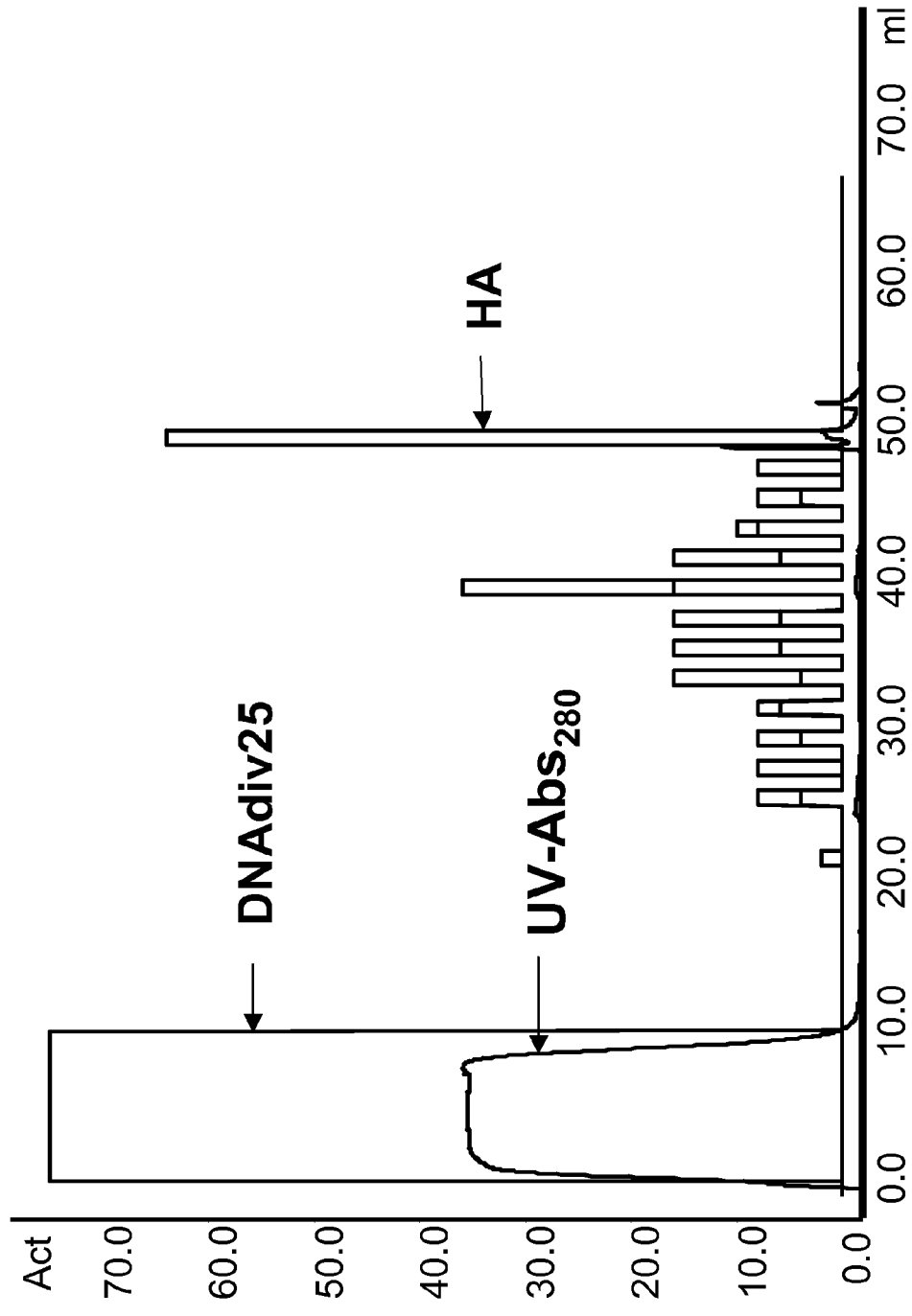
FIG. 1 shows the chromatogram obtained when virus was purified on the commercially available product CELLUFINE™ Sulfate, as described in example 1 below.

The term "extender" means herein a molecule such as a polymer which is provided to distance a ligand from an insoluble carrier. Extenders are also known e.g. as spacers or fluff.

The term "insoluble carrier" means herein any carrier also known as base matrix or support suitable for use in separation methods such as liquid chromatography.

The term "ligand" is used herein in its conventional meaning i.e. as a functional group capable of interacting with a target such as a virus.

The term "separation matrix" means herein an insoluble carrier to which ligands have been attached.

The term "hydrophilic" means herein a water-soluble or water-swellable material, which does not give hydrophobic interactions with proteins.

DETAILED DESCRIPTION OF THE INVENTION

In a first aspect, the present invention relates to a method of preparing a separation matrix comprising at least one insoluble carrier to which sulphate ligands have been attached via extenders, which method comprises coupling, in a first step, of the sulphate ligands to the extenders and, in a subsequent step, attaching the extenders to an insoluble carrier. In a specific embodiment, the extender and carrier are of different materials, such as different kinds of native polymers. Thus, in an illustrative embodiment, the extenders are dextran molecules which are first sulfated and secondly attached to the carrier, such as an agarose carrier. In one embodiment, the sulphate ligands are introduced into the dextran using chlorosulphonic acid. More details regarding the separation matrix prepared according to the invention will be provided below.

In a second aspect, the present invention relates to a separation matrix comprised of at least one insoluble carrier to which sulphate ligands have been attached via extenders, wherein no sulphate ligands are directly attached to the insoluble carrier. In an advantageous embodiment, no sulphate ligands have been directly attached to the insoluble carrier. Put differently, all or substantially all of the ligands are attached to extenders. In a specific embodiment, the extender and carrier are of different materials, such as different kinds of native polymers.

The extenders are advantageously flexible, non-crosslinked polymers, which provide a distance between the carrier and the ligands. The extenders may be comprised of polymers of synthetic or natural origin. In a specific embodiment, the extenders are hydrophilic.

Thus, in one embodiment, the extenders are natural polymers, such as dextran, starch or cellulose, or any mixture thereof. In an advantageous embodiment, the extenders are dextran molecules. Such dextran extenders attached to the carrier may be of a molecular weight in the range of 100-10,000 kDa. In one embodiment, the separation matrix according to the invention comprises extenders having a molecular weight above about 500 kDa, such as a molecular weight in the range of 500-1000 kDa.

In another embodiment, the extenders are synthetic polymers, such as polyacrylamide, polymethacrylamide or polyvinyl ether polymers, or any mixture thereof. The synthetic extenders may have molecular weights similar to those of the above-discussed dextran.

The insoluble carrier may consist of a polymer, preferably a crosslinked polymer, of synthetic or natural origin. In one embodiment, the carrier is made from natural polymers selected from the group consisting of agarose, agar, cellulose, dextran, chitosan, carrageenan, gellan, alginate, and any mixture thereof. In an advantageous embodiment, the insoluble carrier is agarose. The natural polymer carrier can easily be prepared according to standard methods, such as by inverse suspension gelation. Alternatively, the carrier is a commercially available product, such as available agarose or dextran particles from GE Healthcare, Uppsala, Sweden. In an advantageous embodiment, the carrier is dextran or agarose. In an especially advantageous embodiment, the carrier is a crosslinked agarose. In a specific embodiment, the agarose has been rigidified to provide improved flow/pressure properties when used in liquid chromatography. In a specific embodiment, the rigidified agarose was prepared and/or modified to present an improved rigidity in order to with-stand high flow rates, see e.g. U.S. Pat. No. 6,602,990 (Berg), which improved rigidity agarose has been used in the experimental part below (denoted HFA 70). In this context, it is understood that the term "rigidified" refers to a process which provides a more rigid product than conventional cross-linking. In brief, this method comprises modification of the agarose polymers in solution before gelling by adding groups, such as allyl groups, followed by gelling of the agarose and subsequent use of the added groups in cross-linking thereof using conventional methods. The present invention also embraces other rigidified polysaccharide carriers, which may have been prepared as discussed above in the context of agarose.

In an alternative embodiment, the carrier is made from synthetic polymers selected from the group consisting of styrene, styrene/divinylbenzene, divinylbenzene, polyvinyl alcohols, polyacrylamides, polymethacrylamides or polyvinyl ethers.

Further, the insoluble carrier may be porous or non-porous and prepared into any format suitable for separation, such as particles, e.g. essentially spherical particles, a membrane or filter, a capillary, a plug etc. In an advantageous embodiment, the separation matrix is in the form of essentially spherical particles, also known as beads. Such beads may be of an average diameter in the range of 5-500 μm, such as 10-150, or 50-150 μm. In a specific embodiment, the beads have an average diameter of about 100 μm.

In a third aspect, the present invention relates to a method of separating at least one virus from a liquid, either for the purification of a desired virus or to remove one or more viruses from a liquid, such as for the preparation of a liquid product, or for the preparation of e.g. a protein product. Thus, in one embodiment, the present method comprises contacting a liquid comprising said virus with a separation matrix comprising sulfated dextran. In an advantageous embodiment, the separation matrix is the matrix described above. The liquid from which said at least one virus is separated may be a culture liquid, wherein the virus has been produced, such as a fermentation broth or a cell culture supernatant. Alternatively, the liquid may be a biological liquid, such as blood, serum or the like originating from a human or animal. Such liquids may comprise various compounds from which it is desired to separate the virus, such as residues from the recombinant cell culture, proteins e.g. antibodies, peptides, other viruses, nucleic acids, organic compounds such as sugars etc. In another embodiment, the present method is used to separate viruses from cells, such as cells intended for medical, analytical or diagnostic use.

In one embodiment, the present method of separating at least one virus from a liquid comprises
(a) providing a separation matrix comprised of an insoluble carrier to which sulphate ligands have been attached via extenders;
(b) contacting a liquid comprising at least one virus with said separation matrix to allow adsorption of the virus; and optionally,
(c) eluting one or more viruses from the matrix by adding a liquid that releases virus.

In an advantageous embodiment of the present method, the separation matrix is as defined above. Thus, in a specific embodiment, the extenders are dextran molecules having a molecular weight of above about 500 kDa, such as 500-1000 kDa. In an advantageous embodiment, the insoluble carrier is agarose, such as rigidified agarose.

Thus, according to the present invention, virus is separated from other, usually non-desired components of the liquid, such as host cell proteins, residues of nutrients, aggregates etc. In one embodiment of the present method, at least one virus, such as an influenza virus, is separated from nucleic acids, such as DNA or RNA, by contacting a liquid comprising said virus as well as nucleic acid(s) with the above-described separation matrix. In an advantageous embodiment, the liquid is a cell culture liquid wherein virus-producing cells have been cultured.

In another embodiment, the present method separates at least one first virus, such as influenza virus, from at least one other virus species, which is different from said first virus. In a specific embodiment, influenza virus is separated according to the invention from both nucleic acids and other viruses.

The method according to the present invention may be used combined with other steps for viral separation, such as filtration and/or other chromatography steps. Thus, the present invention also embraces any purification protocol comprising one step wherein the separation matrix according to the invention is used to separate virus. In a specific embodiment, such a purification protocol comprises at least one additional step selected from the group consisting of ion exchange, such as cation exchange or anion exchange; hydrophobic interaction chromatography (HIC); reversed phase chromatography (RPC); affinity chromatography; membrane filtration; and phase separation. The skilled person can easily define the appropriate order of such step and select suitable matrices for the capture step, intermediate step(s) and polishing. In this context, it is noted that the order of the listing of possible steps above is no limitation or recommendation of any preferred order of operation.

However, in its broadest aspect, the present invention relates to the use and preparation of a separation matrix which may be used to isolate or separate any animal or plant virus by binding to said virus from a liquid. In an advantageous embodiment, the virus is any animal virus. In this context, the term "animal virus" is understood to mean a virus which will infect vertebrae animals only, in which context the term "animal" includes human.

Thus, the present invention is expected to be useful in the isolation or separation of any virus, such as DNA viruses, RNA viruses and insect viruses.

In one embodiment, the present invention is used to isolate or separate at least one DNA virus selected from the group consisting of parvoviridae, papovaviridae, adenoviridae, iridoviridae, herpesviridae, poxiviridae, and baculoviridae;

In another embodiment, the present invention is used to isolate or separate at least one RNA virus selected from the group consisting of picornaviridae, caliciviridae, reoviridae, togaviridae, flaviviridae, orthomyxoviridae, paramyxoviridae, rhabdoviridae, retroviridae, bunyaviridae, arenaviridae, coronaviridae, and birnaviridae.

In one embodiment, the virus is a DNA virus, such as a virus that belongs to the adenoviridae.

In another embodiment, the virus is an RNA virus, such as a virus selected from the group consisting of the togaviridae family; such as Ross River virus, rubivirus, sindbis virus and rubella virus; the flaviviridae family, such as West Nile virus, yellow fever virus, dengue virus, Japanese encephalitis virus and hepatitis C; the orthomyxoviridae family, such as influenza virus; the paramyxoviridae family, such as measles virus; and the rhabdoviridae family, such as rhabies virus.

In an advantageous embodiment, the orthomyxovirus is influenza virus.

The influenza virus is an enveloped virus around 100-120 nm in size. Dependent on the host it invades, it adds host cell membrane components to the envelope when the virus sheds out from the infected cell. This makes the virus very complex. Two proteins very important for the virus to infect and invade cells are Heamagglutinine (HA) and Neuraminidase (NA). HA is important in the early phase of cell infection as HA is involved in the binding and recognition of sialic acid residues on the cell membrane important for binding and membrane fusion. NA is involved in cleavage and release of the virus from the infected cell as well as penetration of the virus through the mucin layer of the respiratory epithelium. The influenza virus is spread among many animals (birds, pigs, horses) as well as humans and undergoes mutations in the antigenic sites (antigenic drift) as well as changes from one HA subtype to another HA subtype in the virus known as antigenic shifts. This may happen when a cell is infected by two different influenza viruses and their genome segments are exchanged during replication. These mutations inhibit binding of neutralising antibodies why influenza vaccines needs to be prepared on a yearly basis. Today 16 subtypes of HA and 9 subtypes of NA are known in different combinations. Influenza virus is divided into three larger groups (A, B, C) dependent on the nuclear material, but currently only influenza A and B are of interest in humans. The nomenclature for virus isolates are: type (A or B), host species, geographical site, serial number, year of isolation and HA, NA variant in brackets, ex. A/human/Fujian/411/2002 (H3N2).

Thus, in a specific embodiment, the present invention relates to the isolation or separation of human influenza virus, such as influenza A and/or B virus. As discussed above, the influenza virus is known to mutate rapidly, but the skilled person can easily apply the present invention to any one of these virus forms. For example, using routine experimentation, the operating conditions are easily optimised in a liquid chromatography process utilizing a separation matrix according to the invention. Human influenza virus isolated according to the present invention may be used to immunize human beings, in the preparation of a vaccine composition for the immunization of human beings against influenza and/or in the preparation of a viral medicine for treatment of viral infections in human beings. Other uses may be for diagnostic use e.g. to establish whether or not an individual has been infected, for analytical use and for various research purposes. Such a vaccine composition is prepared be combining the isolated vaccine, which may have been attenuated or weakened, with a suitable adjuvant as well as other standard components of a vaccine.

In another embodiment, the present invention relates to the isolation or separation of avian influenza virus, such as the avian H5N1 virus. Avian influenza virus isolated according to the present invention may be used to immunize birds, in the preparation of a vaccine composition for the immunization of birds against influenza and/or in the preparation of a viral medicine for treatment of viral infections in avian species. Other uses may be for diagnostic use e.g. to establish whether or not an avian individual has been infected, for analytical use and for various research purposes. Such a vaccine composition is prepared be combining the isolated vaccine, which may have been attenuated or weakened, with a suitable adjuvant as well as other standard components of a vaccine.

EXAMPLES

The following examples are provided for illustrative purposes only, and should not be construed as limiting the present invention as defined by the appended claims.

Example 1

Separation Medium According to the Invention

The Base Matrix

SEPHAROSE™ 6 Fast Flow (GE Healthcare, Uppsala, Sweden) was chosen as the standard base matrix for the prepared prototypes according to the invention.

Ligands and Surface Modifications

Different prototypes with different ligands/surface modifications were prepared in order to evaluate different virus affinity concepts. The approach that was considered of interest to explore is the interaction between virus and different modified carbohydrate materials. This approach has been used by Chisso Corp. in the product CELLUFINE™ Sulfate.

The Virus

Selected as target was human influenza virus PR 8 A/PR/8/34 (H1N1). The virus was produced in Manin-Darby Canine Kidney (MDCK) cells and virus supernatant from the cultivation was collected by centrifugation and used as test sample. The virus was cultivated and prepared in accordance with standard procedures.

Screening Method

The ability of the prepared media to separate virus material from DNA was tested by packing the media into HR5/5 columns (GE Healthcare, Uppsala, Sweden) which were coupled to an ÄKTA™ FPLC system (GE Healthcare, Uppsala, Sweden) equipped with an UV detector and fraction collector. The virus containing material was applied on the different prototypes and fractions were collected using a NaCl gradient for elution. The fractions were subsequently analysed regarding DNA, protein and virus content. Columns were cleaned in place (CIP) with 1 M NaOH after runs. Operating conditions were according to standard procedures, wherein the exact buffer conditions were selected according to what has previously been described as suitable conditions for this virus and/or the media to be tested.

Analytical Methods

Hemaglutinin content was analysed using two different methods, one based on the agglutination of red blood cells (RBC) from hen, and another method based on an ELISA. DNA was analysed using Molecular Probes PICOGREEN® fluorescence method (Invitrogen). The host cell proteins (HCP) were detected using BCA™ protein kit (PIERCE). Further details regarding analytical methods were in accordance with standard procedures.

Results Example 1

Introduction

In order to find a suitable construction, several different constructions were prepared based on different carbohydrate graftings in combination with sulfate.

Synthesis

Several of the intended prototypes could be prepared using commercially available starting materials in combination with well known standard coupling technologies. The sulfate groups were introduced using chlorosulfonic acid. For several of the constructions, SEPHAROSE™ 6 Fast Flow base matrix was considered as useful for the initial experiments, but for some constructions other base matrices were investigated. For comparison also a prototype carrying sulfonate groups on the dextran grafting only was prepared.

The prototypes that were eventually prepared are described in table 1 below. Included in the study was also the commercially available media Heparin SEPHAROSE™ 6FF (GE Healthcare, Uppsala, Sweden), which is a SEPHAROSE™ 6 Fast Flow base matrix grafted with heparin.

TABLE 1

Properties of prepared pseudo affinity prototypes

| ID. (J. page) | Construction | Grafting (mg/mL) | Ionic cap. (μmol/mL) |
|---|---|---|---|
| U1404040 | SEPHAROSE ™ 6FF, epoxy activation, dextran sulphate with Mw 500 kD | N.D. | 30 |
| U1404038 | SEPHAROSE ™ 6FF, epoxy activation, dextran sulphate with Mw 500 kD | N.D. | 108 |
| U1404049 | SEPHAROSE ™ 6FF, epoxy activation, cellulose sulphate | N.D. | 15 |
| U1404053 | SEPHAROSE ™ 6 FF, dextran grafting Mw 40 kD, coupling with chloro sulfonic acid | 19 | 33 |
| U1404051 | SEPHAROSE ™ 6 FF, dextran grafting Mw 40 kD, coupling with chloro sulfonic acid | 19 | 470 |
| U1404070 | SEPHAROSE ™ 6 FF, coupling with chloro sulfonic acid | N.D. | 66 |
| U1404061 | SEPHADEX ™ G 50, coupling with chloro sulfonic acid | N.D. | 70 |

N.D. = Not Determined.

Chromatography

Prototypes were tested chromatographically using 10 mM sodium phosphate, pH 7.4 and a gradient from 0-100% 1.5 M NaCl in 10 mM phosphate, pH 7.2, during 20 column volumes for elution. Fractions were collected and analysed with respect to virus, protein (hemaglutinin) and DNA content.

CELLUFINE™ Sulfate was used as bench marking material.

Evaluation

For several of the prototypes, namely U1404049 and U1404053 there was no substantial retardation of the virus material at the testing conditions chosen and accordingly these constructions were left without further consideration. With prototype U1404051 the virus material was retarded, and also eluted in salt gradient, but the eluted material was contaminated with excessive amounts of protein material as measured by UV at 280 nm.

The SEPHADEX™ G 50 bead carrying sulfate groups (U1404061) did retard the virus material while the DNA was found in the flow through.

The Heparin 6 FF material did also retard the virus material but also retarded the DNA.

Both DNA and virus were eluted at the same position in the gradient, and accordingly have no separation of these two materials even though elution peaks were narrow. For the prototypes based on agarose beads with different levels of sulphated dextran (U1404040, U1404038) a chromatographic behaviour similar to the behaviour of CEL-LUFINE™ Sulfate was found (FIG. 1).

A summary of the behaviour of the different constructions regarding virus retardation under the test conditions is presented in Table 4 below.

TABLE 4

Overview of construction composition and their behaviour regarding retardation of virus material

| Construction | Virus retardation |
|---|---|
| Sulfate on dextran grafting only on agarose bead | + |
| Sulfate on dextran bead | + |
| Sulfate on agarose bead | − |
| Sulfate on both agarose bead and dextran grafting | +/− |

TABLE 4-continued

Overview of construction composition and their behaviour regarding retardation of virus material

| Construction | Virus retardation |
|---|---|
| Sulfonate on dextran grafting only on agarose bead | − |
| Sulfonate on both agarose bead and dextran grafting | − |
| Sulfate on cellulose grafting only on agarose bead | − |
| Heparin on agarose | +/− |

+ denotes virus retardation,
− denotes no virus retardation, or other not preferred behaviour.

As can be noted, it appears that sulfate in combination with dextran is a preferred composition for separation of human influenza virus and DNA under the tested chromatographic conditions. Also heparin gives a retardation of virus material, but no separation from DNA. It should be noted that sulfate on agarose (U1404053 and U1404051) apparently has a negative influence on virus binding/separation. For the prototype U1404038, a preliminary investigation of the binding capacity indicated that the capacity was in level with or above the capacity of Q SEPHAROSE™ XL.

Additional Chromatography

Since it was considered of interest to transfer the findings made here regarding combining agarose beads and sulfated dextran for the separation of virus material to a recently developed base matrix "HFA 70", prepared as described in U.S. Pat. No. 6,602,990 (Berg), prototypes with this base matrix and different loadings of sulfated dextran were prepared (Table 3).

TABLE 3

| Data for prototypes based on sulphated dextran on HFA 70 matrix | | |
|---|---|---|
| ID. (J. page) | Construction | Ionic cap. (μmol/mL) |
| 1689044A | HFA 70, epoxy activation, dextran sulphate with Mw 500 kD | 34 |
| 1689044B | HFA 70, epoxy activation, dextran sulphate with Mw 500 kD | 94 |
| 1689044C | HFA 70, epoxy activation, dextran sulphate with Mw 500 kD | 186 |

The chromatographic behaviour for these prototypes was comparable for the prototypes based on SEPHAROSE™ 6 FF base matrix.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of liquid chromatography for purifying an influenza virus from a cell liquid comprising virus as well as nucleic acid(s), which method comprises:

(a) providing a separation matrix comprised of a base matrix to which sulphate ligands have been attached via extender molecules, wherein the sulphate ligands were coupled to the extender molecules before the attachment thereof to the base matrix, and wherein the extender molecules are dextran molecules having a molecular weight of above 500 kDa;

(b) contacting the cell liquid with said separation matrix to allow adsorption of the influenza virus, and optionally;

(c) eluting the influenza virus from the matrix by adding a liquid that releases said virus.

2. The method of claim 1, wherein the virus is separated from nucleic acids in said liquid.

3. The method of claim 2, wherein the nucleic acid is DNA.

4. The method of claim 1, wherein the liquid is a cell culture supernatant.

5. The method of claim 1, wherein the base matrix is an agarose carrier.

6. The method of claim 1, wherein the influenza virus is separated from other virus than influenza.

* * * * *